(12) United States Patent
Peyman (10) Patent No.: US 11,020,270 B1
(45) Date of Patent: Jun. 1, 2021

(54) VITRECTOMY INSTRUMENT AND A SYSTEM INCLUDING THE SAME

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 16/445,147

(22) Filed: Jun. 18, 2019

Related U.S. Application Data (60) Provisional application No. 62/686,322, filed on Jun. 18, 2018, provisional application No. 62/690,166, filed on Jun. 26, 2018.

(51) Int. Cl.
*A61F 9/007* (2006.01)

(52) U.S. Cl.
CPC ...... *A61F 9/00745* (2013.01); *A61F 9/00763* (2013.01); *A61B 2217/005* (2013.01); *A61F 9/00754* (2013.01)

(58) Field of Classification Search
CPC .............. A61F 9/00745; A61F 9/00763; A61F 9/00754; A61B 2217/005; A61B 17/320758; A61B 2017/320775; A61B 17/320783; A61B 17/32; A61B 17/32002; A61B 17/320016; A61B 17/320068; A61B 2017/320004; A61B 2017/320008; A61B 2017/320012; A61B 2017/320024; A61B 2017/320028; A61B 2017/320032; A61B 2017/32007; A61B 2017/320074; A61B 2017/320075; A61B 2017/320077; A61B 2017/32008
See application file for complete search history.

(56) References Cited

U.S. PATENT DOCUMENTS

| | | |
|---|---|---|
| 4,019,514 A | 4/1977 | Banko |
| 4,099,529 A | 7/1978 | Peyman |
| 4,428,748 A | 1/1984 | Peyman et al. |
| 4,551,129 A | 11/1985 | Coleman et al. |
| 5,487,725 A | 1/1996 | Peyman |
| 5,547,473 A | 8/1996 | Peyman |
| 5,591,160 A | 1/1997 | Reynard |
| 5,690,663 A | 11/1997 | Stephens |
| 5,716,363 A * | 2/1998 | Josephberg ......... A61F 9/00763 604/22 |

(Continued)

*Primary Examiner* — George J Ulsh
*Assistant Examiner* — Andrew P. Restaino
(74) *Attorney, Agent, or Firm* — The Law Office of Patrick F. O'Reilly III, LLC (57) ABSTRACT

A vitrectomy instrument and a system including the same are disclosed herein. The vitrectomy instrument includes a handpiece having an outer tube and an inner tube coaxially disposed in the outer tube, the inner tube being slidably displaceable relative to the outer tube; a cutting power generator operatively coupled to the inner tube, the cutting power generator configured to reciprocably drive the inner tube for shearing tissue and/or vitreous; and an ultrasonic generator operatively coupled to the inner tube, the ultrasonic generator configured to vibrate the inner tube for vibratory fragmentation and/or cutting of the tissue and/or the vitreous. The vitrectomy system may include the vitrectomy instrument together with a support sleeve for supporting the vitrectomy instrument to provide increased rigidity to the needle of the vitrectomy instrument.

7 Claims, 5 Drawing Sheets

(56) References Cited

U.S. PATENT DOCUMENTS

| | | | |
|---|---|---|---|
| 5,725,514 | A | 3/1998 | Grinblat et al. |
| 5,911,699 | A * | 6/1999 | Anis ............... A61F 9/00745 |
| | | | 604/22 |
| 6,395,294 | B1 | 5/2002 | Peyman |
| 6,936,053 | B1 | 8/2005 | Weiss |
| 7,783,346 | B2 | 8/2010 | Smith et al. |
| 8,231,544 | B2 | 7/2012 | Mark |
| 8,979,867 | B2 | 3/2015 | Peyman |
| 9,216,067 | B2 | 12/2015 | Peyman |
| 2007/0129732 | A1 * | 6/2007 | Zacharias ........... A61F 9/00763 |
| | | | 606/107 |
| 2007/0225727 | A1 | 9/2007 | Matsuhisa et al. |
| 2008/0086160 | A1 | 4/2008 | Mastri et al. |
| 2011/0112377 | A1 | 5/2011 | Papac et al. |
| 2011/0230728 | A1 | 9/2011 | Artsyukhovich et al. |
| 2012/0035425 | A1 | 2/2012 | Schaller |
| 2012/0083793 | A1 | 4/2012 | Oster |
| 2012/0209303 | A1 * | 8/2012 | Frankhouser ........ A61B 90/06 |
| | | | 606/169 |
| 2013/0079806 | A1 | 3/2013 | Peyman |
| 2013/0245659 | A1 * | 9/2013 | Robertson ........ A61B 17/22004 |
| | | | 606/169 |
| 2013/0253557 | A1 * | 9/2013 | Urich ............... A61B 17/3209 |
| | | | 606/169 |
| 2017/0165114 | A1 * | 6/2017 | Hallen ............... A61F 9/00781 |
| 2017/0215912 | A1 * | 8/2017 | Truckai ............ A61B 17/00234 |

* cited by examiner

FIG. 1

Detail "A"

VITRECTOMY INSTRUMENT AND A SYSTEM INCLUDING THE SAME

CROSS-REFERENCE TO RELATED APPLICATIONS

This patent application claims priority to U.S. Provisional Patent Application No. 62/686,322, entitled "Vitrectomy Instrument And A System Including The Same", filed on Jun. 18, 2018; and further claims priority to U.S. Provisional Patent Application No. 62/690,166, entitled "Supporting Sleeve For A Vitrectomy Instrument And A System Including The Same", filed on Jun. 26, 2018, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a vitrectomy instrument and a system including the same. More particularly, the invention relates to a vitrectomy system that includes a vitrectomy instrument that is capable of simultaneously cutting and applying ultrasonic energy to tissue in the eye. The system may further include a supporting sleeve for the vitrectomy instrument that enables a vitrectomy instrument with a long needle to be inserted into the eye of a patient without substantial deflection and/or deformation of the needle.

2. Background

In order to provide better access to the retina, it is often necessary to perform a vitrectomy. A vitrectomy is a surgical procedure undertaken by a specialist (e.g., a retinal surgeon) whereby the vitreous humor gel that fills the eye cavity is removed to provide better access to the retina.

Many conventional instruments are used to perform vitrectomy procedures. However, these conventional instruments suffer from numerous limitations and drawbacks. First of all, some of these conventional instruments undesirably heat the tissue in contact with the instrument, thus deleteriously burning the tissue of the patient. In order to prevent this burning of the adjacent tissue, these conventional instruments often require a plastic insulating sleeve to be placed around the needle of the instrument, thus making them more bulky and necessitating a larger incision for the initial insertion of the instrument needle.

Therefore, what is needed is a vitrectomy instrument that facilitates the cutting of tissue or vitreous without the undesirable excessive heating and resulting burning of the tissue surrounding the instrument during the procedure. Moreover, a vitrectomy instrument is needed that does not require the use of a plastic insulating sleeve to be placed around the needle of the instrument, thus permits a small incision to be made for the insertion of the instrument. Furthermore, there is a need for a vitrectomy system that includes the vitrectomy instrument which provides separate irrigation means so as to minimize the size of the needle of the vitrectomy instrument.

In addition, many conventional instruments are too flexible once they are inserted inside the eye (e.g., instruments having 25 gauge and 27 gauge tips). As such, due to the overly flexible nature of these instrument tips, the slightest pressure that moves the eye during surgery also can bend the shaft of the cutter in one direction at the incision site while the inside portion of the shaft moves in another direction. This movement can be disturbing to an operator who does not expect motion in an opposite direction from that which was intended and can cause injury to the fine structure of the lens or the retina. Also, in myopic eyes having a longer axial length than normal, a needle having a longer (36-38 mm) than normal shaft (e.g., 30 mm) is required. This makes the conventional instruments flimsy and not desirable.

Therefore, what is needed is a support sleeve for a vitrectomy instrument that structurally supports the flexible needle of the instrument so as to prevent the needle from moving and/or bending during surgery. Moreover, a support sleeve for a vitrectomy instrument is needed that enables a vitrectomy instrument with a long needle to be more effectively used in myopic eyes, which have a longer axial length than normal eyes. Furthermore, there is a need for a vitrectomy system that includes a rigid support sleeve for enabling a vitrectomy instrument with a long needle to be used in an eye without excessive deflection and/or bending thereof.

BRIEF SUMMARY OF EMBODIMENTS OF THE INVENTION

Accordingly, the present invention is directed to a vitrectomy instrument and a system including the same that substantially obviates one or more problems resulting from the limitations and deficiencies of the related art.

In accordance with one or more embodiments of the present invention, there is provided a vitrectomy instrument that includes a handpiece having an outer tube and an inner tube coaxially disposed in the outer tube, the inner tube being slidably displaceable relative to the outer tube; a cutting power generator operatively coupled to the inner tube, the cutting power generator configured to reciprocably drive the inner tube for shearing tissue, vitreous, silicone oil, and/or perfluorocarbon liquid; and an ultrasonic generator operatively coupled to the inner tube, the ultrasonic generator configured to vibrate the inner tube for vibratory fragmentation and/or cutting of the tissue, the vitreous, the silicone oil, and/or the perfluorocarbon liquid.

In a further embodiment of the present invention, the outer tube comprises a body and a closed end tip, the body of the outer tube including a sidewall extending in an axial direction from the closed end tip, the body of the outer tube defining a linear passageway closed at a distal end by the closed end tip; and the outer tube further comprises an opening disposed in the sidewall of the body, the opening being disposed proximate to the closed end tip of the outer tube, and the opening being configured to enable cutting of the tissue, the vitreous, the silicone oil, and/or the perfluorocarbon liquid.

In yet a further embodiment, the cutting power generator is separate from the ultrasonic generator such that the cutting power generator and the ultrasonic generator are capable of being simultaneously or individually operated.

In still a further embodiment, the ultrasonic generator is configured to produce signals in a frequency range of 20,000 cycles per second or greater for the vibratory fragmentation and/or cutting of the tissue, the vitreous, the silicone oil, and/or the perfluorocarbon liquid by the inner tube.

In yet a further embodiment, the vitrectomy instrument further comprises an aspiration device operatively coupled to the handpiece, the aspiration device configured to generate an aspiration force for removing cut tissue and/or cut vitreous through the inner tube.

In still a further embodiment, the aspiration device comprises a suction pump or a rotary pump for generating the aspiration force for removing the cut tissue and/or the cut vitreous through the inner tube of the handpiece.

In yet a further embodiment, the aspiration device comprises a rotary or roller type peristaltic compression of a flexible aspiration tube whereas a venturi system creates a vacuum by the flow of a compressed air or a gas over a nozzle connected to a closed drainage vacuum, thereby generating the aspiration force for removing the cut tissue, cut vitreous and/or fragmented silicone oil through the inner tube of the handpiece.

In still a further embodiment, the handpiece is not provided with irrigation means so as to enable the diameter of the handpiece to be made as small as possible.

In accordance with one or more other embodiments of the present invention, there is provided a support sleeve for a vitrectomy instrument. The support sleeve includes an elongate tubular body having a first end and a second end disposed opposite to the first end, the elongate tubular body including a peripheral sidewall and a central passageway disposed through the elongate tubular body, the central passageway of the elongate tubular body configured to receive a needle of a vitrectomy instrument therein. In these one or more embodiments, the elongate tubular body of the support sleeve is formed from a material that is substantially more rigid than a material used to form the needle of the vitrectomy instrument so as to generally prevent the needle of the vitrectomy instrument from deflecting and/or deforming when the needle is supported in the central passageway of the elongate tubular body of the support sleeve.

In a further embodiment of the present invention, the first end of the elongate tubular body comprises a flared end portion configured to prevent the support sleeve from entering too deep into an eye, and wherein the second end of the elongate tubular body comprises a pointed tip configured to cut through tissue of the eye.

In yet a further embodiment, the material forming the elongate tubular body of the support sleeve is substantially transparent to visible light from 400-800 nanometers.

In still a further embodiment, the support sleeve further comprises an illumination device operatively coupled to the elongate tubular body such that the illumination device is capable of providing illumination to an inside portion of an eye through at least a portion of the elongate tubular body.

In yet a further embodiment, the elongate tubular body comprises an opaque coating from the first end to an exposed tip at the second end so as to enable the exposed tip to function as a localized light source.

In still a further embodiment, the opaque coating of the elongate tubular body is formed by coating the peripheral sidewall of the elongate tubular body with a black material.

In yet a further embodiment, the material forming the elongate tubular body of the support sleeve comprises one of: (i) metal glass, (ii) amorphous glass, (iii) palladium alloy, (iv) zirconium alloy, (v) aluminum oxynitride, (vi) magnesium aluminate spinel, (vii) single crystal aluminum oxide, (viii) aluminum nitryloxyde, and (ix) stainless steel.

In still a further embodiment, the elongate tubular body is formed by three dimensional (3D) printing.

In yet a further embodiment, the elongate tubular body has a diameter of a 25-30 gauge needle.

In accordance with yet one or more other embodiments of the present invention, there is provided a vitrectomy system includes a vitrectomy instrument and a support sleeve for supporting the vitrectomy instrument. The vitrectomy instrument includes a needle with an elongate outer tube with a body having a closed end tip, the body of the elongate outer tube including a sidewall extending in axial direction from the closed end tip, the body of the elongate outer tube defining a linear passageway closed at a distal end by the closed end tip, the elongate outer tube further including an opening disposed in the sidewall of the body, the opening being disposed proximate to the closed end tip of the body, and the opening being configured to enable cutting of vitreous or tissue; and an elongate inner tube arranged concentrically within the elongate outer tube, the elongate inner tube being configured to oscillate so as to be capable of cutting the vitreous or the tissue that enters the opening in the body of the elongate outer tube. The elongate outer tube of the needle is formed using a first material that deflects and/or deforms when the needle is inserted into an eye of a patient. The support sleeve for the vitrectomy instrument includes an elongate tubular body having a first end and a second end disposed opposite to the first end, the elongate tubular body including a peripheral sidewall and a central passageway disposed through the elongate tubular body, the central passageway of the elongate tubular body configured to receive the needle of the vitrectomy instrument therein. The elongate tubular body of the support sleeve is formed from a second material that is substantially more rigid than the first material forming the needle of the vitrectomy instrument so as to generally prevent the needle of the vitrectomy instrument from deflecting and/or deforming when the needle is supported in the central passageway of the elongate tubular body of the support sleeve (e.g., the first material forming the needle of the vitrectomy instrument may have a Brinell hardness of between 160 and 300, whereas the second material of the elongate tubular body of the support sleeve may have a Brinell hardness of greater than 900).

In a further embodiment of the present invention, the second material forming the elongate tubular body of the support sleeve is substantially transparent to visible light from 400-800 nanometers.

In yet a further embodiment, the first material forming the elongate outer tube of the needle comprises stainless steel, and the second material forming the elongate tubular body of the support sleeve comprises one of: (i) metal glass, (ii) amorphous glass, (iii) palladium alloy, (iv) zirconium alloy, (v) aluminum oxynitride, (vi) magnesium aluminate spinel, (vii) single crystal aluminum oxide, (viii) aluminum nitryloxyde, and (ix) stainless steel.

In still a further embodiment, the elongate tubular body of the support sleeve is formed by three dimensional (3D) printing.

In yet a further embodiment, the elongate tubular body of the support sleeve has a diameter of a 25-30 gauge needle.

In still a further embodiment, the vitrectomy system further comprises a sleeve illumination device operatively coupled to the elongate tubular body of the support sleeve such that the sleeve illumination device is capable of providing illumination to an inside portion of an eye through at least a portion of the elongate tubular body.

In yet a further embodiment, the sleeve illumination device is connected to the elongate tubular body of the support sleeve at a portion of the support sleeve that does not enter the eye.

In still a further embodiment, the sleeve illumination device is disposed inside the elongate tubular body of the support sleeve.

In yet a further embodiment, the eye of a patient comprises a myopic eye having a distance of greater than 35 millimeters from the cornea to the retina, and wherein the elongate inner tube is configured to reach a posterior portion of the myopic eye.

In still a further embodiment, the length of the intraocular portion of the elongate tubular body of the support sleeve is between approximately 26 and 30 millimeters, and the length of the needle of the vitrectomy instrument is between approximately 36 and 38 millimeters in order to easily reach the posterior portion of the myopic eye without the need of pressing on the wall of the myopic eye or otherwise distorting the myopic eye.

In yet a further embodiment, the elongate inner tube of the vitrectomy instrument is configured to remove the cut vitreous or the cut tissue by the vitrectomy instrument applying an aspiration force to the cut vitreous or the cut tissue.

In still a further embodiment, the aspiration force applied by the vitrectomy instrument is configured to draw the cut vitreous or the cut tissue through the opening disposed in the sidewall of the body of the elongate outer tube.

In yet a further embodiment, the support sleeve is configured to contain the closed end tip of the needle of the vitrectomy instrument when the vitrectomy instrument is being removed from the eye so as to prevent the closed end tip from contacting and contaminating healthy tissue in the eye.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

In an illustrative embodiment, the vitrectomy system may include a handpiece 10 having an operating needle 12 with a tip 14 (see FIG. 1), a foot control switch and a central control unit. In the illustrative embodiment, fluid for irrigation is delivered separately from the handpiece 10 from a supply bottle, which is connected to a first tube which passes through an on-off valve and then through a second tube for supplying irrigation fluid to the operating site. An irrigation control may be provided with a knob for also controlling the irrigation flow to the operating site.

Aspiration may be provided by a collecting bottle which receives the aspirated fluid from a first tube which is supplied from a peristaltic pump that is connected to a second tube. Second tube may be connected to a suitable coupling which provides aspiration from the handpiece 10. An aspiration control may be connected to the peristaltic pump and the foot switch may have an aspiration control switch with an on-off contact button that can be controlled by the surgeon's foot. The foot control also may have an irrigation control switch which can be controlled by the on-off switch contact button by the surgeon's foot. By pivoting down on the foot plate relative to its base, a momentary control switch may be actuated to turn on the ultrasonic power as needed. The various electrical cables from the foot control may be housed in a cable, connected to the central control unit.

Ultrasonic power may be applied to the inner tube 16 of the handpiece 10 (see FIG. 1) from an ultrasonic power source that has an output power meter and a control knob and through a cable which connects to a handpiece cable, which has two conductors connected to the ultrasonic motor to drive the inner tube 16. Sonic cutting power may be supplied from a sonic power generator which provides an output through an indicating meter and has a control knob through leads, and through a first cable connected to a second cable which carries a pair of conductors which are connected to drive the hollow inner tube 16 contained inside the outer tube 18 of the needle 12 and the handpiece 10 to provide chopper power in an oscillatory translational manner. In the illustrative embodiment, there is no direct electrical connection to the tip of the instrument, so there is no electrical shock hazard.

Figure 1:
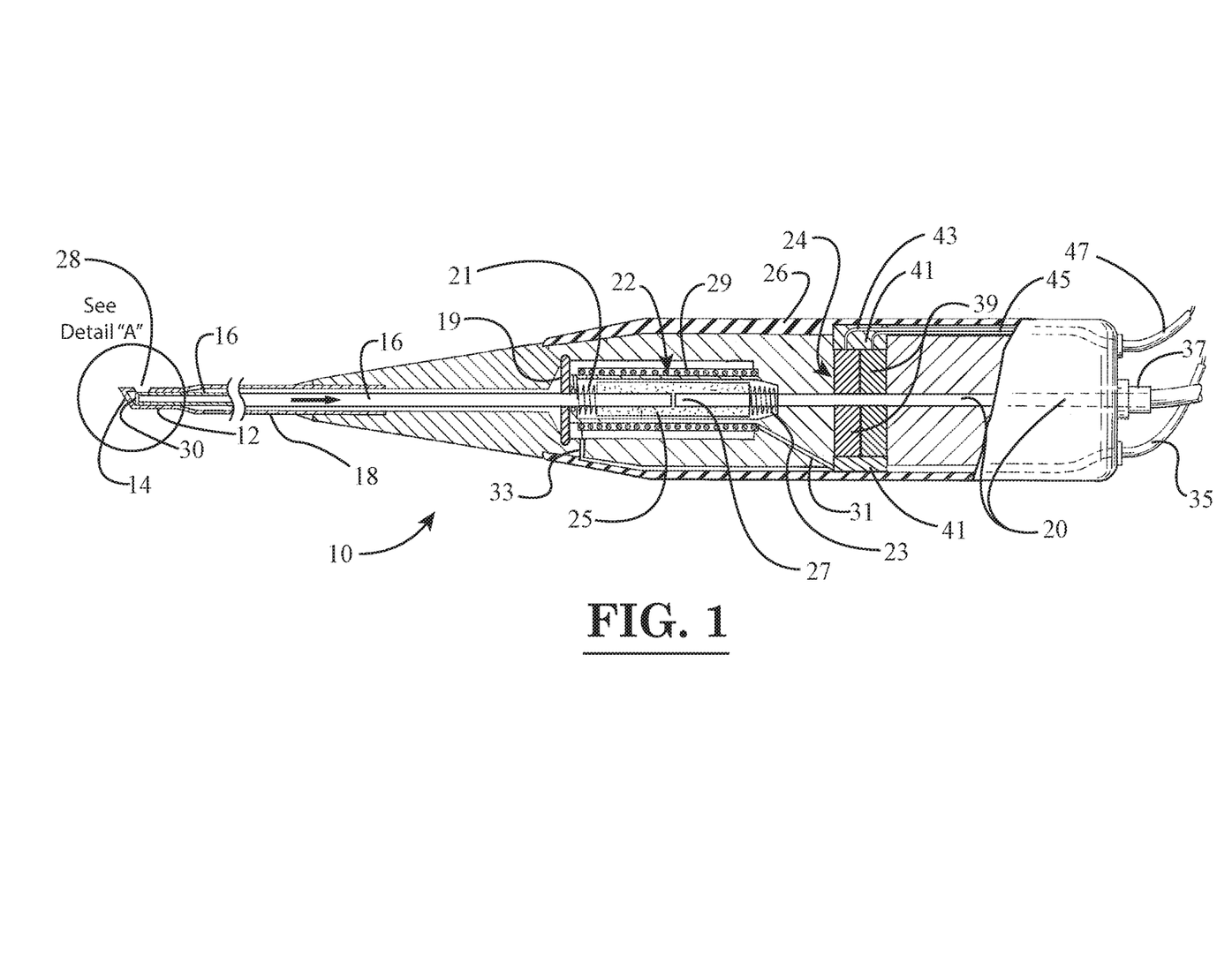
FIG. 1 is a diagrammatic, partial longitudinal sectional view of a vitrectomy instrument, according to an embodiment of the invention.
Figure 2:
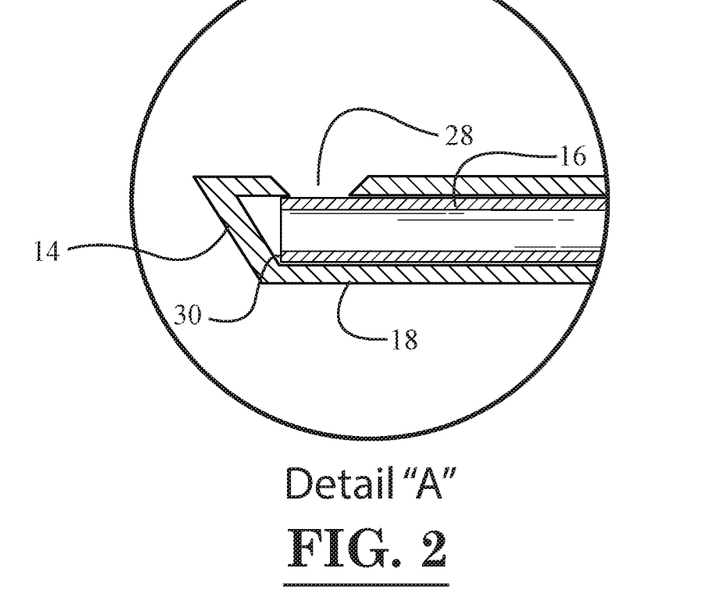
FIG. 2 is a sectional view of an end portion of an outer tube of the vitrectomy instrument of FIG. 1 (Detail "A")

FIG. 1 comprises a partial longitudinal sectional view through the handpiece 10. In the illustrative embodiment, the handpiece 10 may have an outer plastic coating disposed on a cylindrical body 26 formed by one or more cylindrical portions. As shown in FIG. 1, the handpiece 10 further comprises the ultrasonic system 24 that forms the ultrasonic motor for vibrating the inner tube 16. In the illustrative embodiment, the ultrasonic system 24 may comprise a plurality of separated piezoelectric disc members 39. As shown in FIG. 1, the piezoelectric disc members 39 are vibrationally-isolated from the cylindrical body 26 by damping material 41 such that just the inner tube 16 of the instrument is vibrated by the piezoelectric disc members 39. Ultrasonic power for the ultrasonic system 24 may be supplied via conductors 43, 45 that are attached to the cylindrical body of the handpiece 10, and are connected to electrical power cable 47. The needle portion 12 could be a fixed part of the handpiece 10 as in a disposable hand unit. The outer tube 18 of the handpiece 10 is mounted in the front end of the cylindrical body 26 and is formed with the end tip 14 and a chopper and aspiration opening 28 closely adjacent the end tip 14 (see FIGS. 1 and 2). In addition, in some alternative embodiments, an irrigating opening also may be formed in the outer tube 18. The hollow inner tube 16 is mounted concentrically within the outer tube 18 and is oscillated back and forth so that its end 30 performs a shearing action as the inner tube 16 is oscillated so as to cut tissue which extends into the opening 28 of the handpiece needle 12.

Now, the sonic chopper power generator 22 of the handpiece 10, which generates the oscillatory cutting action of the inner tube 16, will be described. In the illustrative embodiment, the proximal end of inner tube 16 may be received in one end of a powdered iron core 25, which is formed with a central opening 27, and which is mounted in a cylindrical opening formed in the cylindrical body of the handpiece 10. The handpiece 10 may further comprise a circular diaphragm 19 mounted at the end of the cylindrical opening of the cylindrical body and may have a central opening through which the inner tube 16 extends and an O-ring seal may form a fluid seal between the inner tube 16 as well as form a guide for the inner tube 16. A pair of springs 21, 23 may be respectively mounted at either end of the power core 25 to bias it generally toward the center of the cavity and an energizing coil 29 of generally cylindrical form may fit about the iron core 25 within the cavity. In the illustrative embodiment, power may be supplied to the energizing coil 29 via input leads 31, 33 routed through cable 35 to the sonic chopper power generator 22. In one or more alternative embodiments, the sonic chopper power generator 22 of the handpiece 10 may be in the form of a piezoelectric system.

In the illustrative embodiment, the pair of springs 21, 23 of the sonic chopper power generator 22 may be made of phosphor bronze material and may be helical in shape. When the iron core 25 is driven by the alternating current in the energizing coil 29 which produces a magnetic field, the springs 21, 23 maintain pressure on both ends of the core 25 so that it will oscillate back and forth about a centered position, thus causing the inner tube 16 to chop tissue with its sharp outer end 30.

For aspiration, in the illustrative embodiment, a flexible supply tube 20 may be received in the end of the iron core 25 opposite the inner tube connection and extend through one of the springs 23 and axially in a central location of the instrument body. The flexible tube 20 may then pass through a coupling 37 in the cylindrical body 26 of the handpiece 10 and be routed outside of the handpiece 10, thereby providing the aspiration passage.

As described above, in the illustrative embodiment, irrigation is provided through separate tubing routed to the eye or other organ. In the illustrative embodiment, the irrigating fluid passes from the supply bottle, through the first and second tubes and a valve to point of delivery at the eye or other organ.

In the illustrative embodiment, the aspiration fluid and debris passes through the aspiration opening 28, then through the center of the inner tube 16, through the opening of the iron core 25, then through the flexible aspirating tube 20 leading out of the handpiece 10. The cutting opening 28 in the outer tube 18 can be round, oval, angled, notched or a combination thereof.

In the illustrative embodiment, the system could include a light source (e.g., a fiber optic device) for illumination coupled to the irrigation tube or a separate light source.

In one embodiment, the inner tube 16 may have its end 30 formed with an inverse taper end sharpened so as to facilitate superior shearing and cutting as it moves past the hole 28 of the outer tube 18.

In the use of the system, the surgeon can selectively apply irrigation fluid to the eye or other organ by closing the irrigation control switch on the foot control so that fluid passes through the separate tubing to the eye or other organ. Aspiration can be controlled with the aspiration control switch on the foot control which operates the peristaltic pump, such that aspiration is produced through the aspiration opening 28 of the needle 12, through the central opening of the inner tube 16, through the passage, flexible tube of the handpiece 10, and through external tubes to the collection container.

When the surgeon desires ultrasonic power, he or she can apply power to the ultrasonic motor through leads, thereby driving the inner tube 16 so as to provide ultrasonic fragmenting.

If the surgeon desires to chop with the end 30 of the inner tube 16, he or she applies power to the energizing coil 29 which drives the inner tube 16, thus causing chopping and cutting of material through the opening 28.

It is to be realized that the surgeon may simultaneously utilize ultrasonic power to fragment with the inner tube 16 as well as sonic chopper power to cut with the cutting action of the inner tube 16, or he or she may elect to use only one of the two cutting modes. The surgeon may also selectively irrigate and aspirate as he or she desires.

Figure 4:
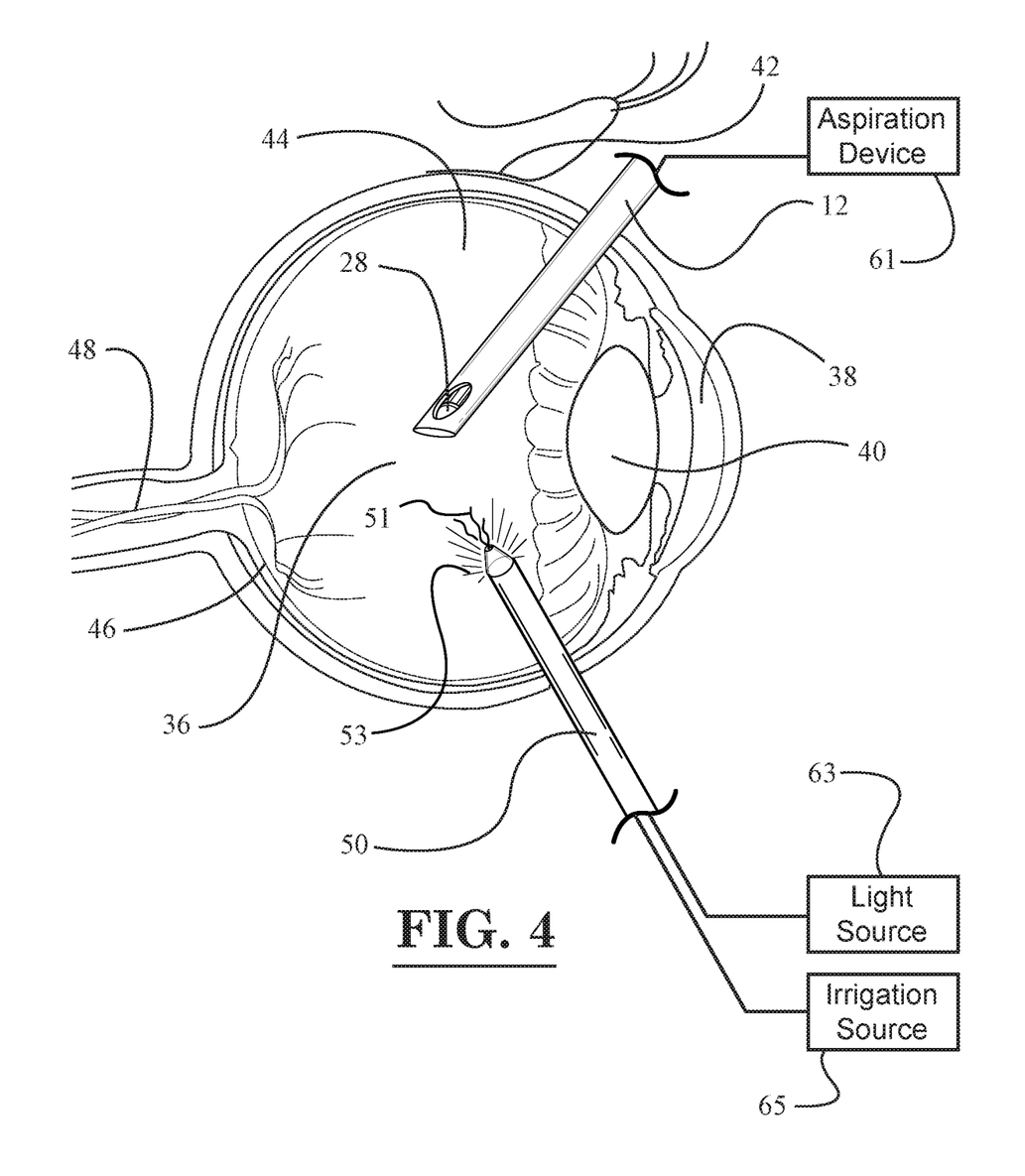
FIG. 4 is a side cross-sectional view of an eye having a surgical procedure performed thereon, which illustrates the use of a vitrectomy instrument for cutting and ultrasonic fragmentation of the vitreous humour, and an infusion and illumination tube for irrigating and illuminating the eye during the surgical procedure.

For example, as shown in the illustrative embodiment of FIG. 4, an eye 36, which includes a cornea 38, a lens 40, a conjunctiva 42, a vitreous cavity 44, a retina 46, and an optic nerve 48, is undergoing a surgical procedure. As part of this procedure, the conjunctiva 42 is cut, and the needle 12 of a vitrector handpiece 10 is inserted into the vitreous cavity 44 of the eye 36 for cutting and ultrasonic fragmenting of the vitreous humour or high viscosity silicone oil. In FIG. 4, the handpiece 10 is operatively connected to an aspiration device 61 for aspirating the cut tissue from the eye 36. In addition, as shown in FIG. 4, an infusion and illumination tube 50 may be inserted into the pars plana area of the eye 36 for irrigating with a liquid 51 and illuminating the eye 36 with light 53 during the surgical procedure. In FIG. 4, the infusion and illumination tube 50 is operatively connected to a light source 63 and an irrigation source 65.

Although the illustrative embodiment provides for aspiration through the concentric tubes 16, 18 of the handpiece 10, it is to be realized that a separate aspiration device could be utilized during surgery.

In an alternative embodiment, rather than being provided with the generally open end 30, the inner tube 16 may be provided with a side opening which at times mates with opening 28 in the outer tube 18 so that cutting can occur as the inner tube opening moves relative to the outer tube opening 28. In this alternative embodiment, a motor may be connected to inner tube by a shaft to rotate or oscillate the inner tube. Ultrasonic energy would also be applied to the inner tube 16 as in the illustrative embodiment described above so that simultaneous or alternate cutting by ultrasonic or a mechanical power can be utilized.

Figure 3A:
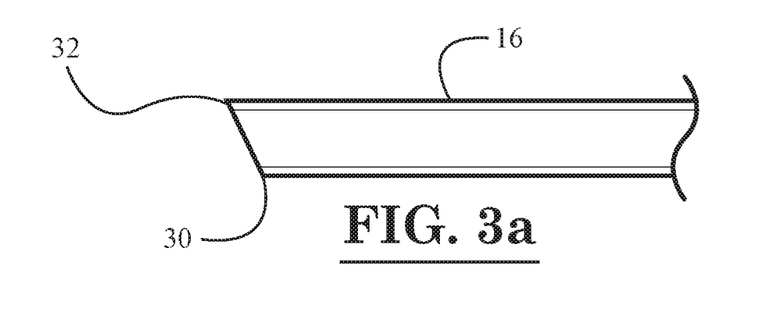
FIG. 3a is a perspective view of a first alternative type of end portion of an inner tube of the vitrectomy instrument of FIG. 1.

In one embodiment, a medical cutting instrument for ophthalmic vitrectomy having an inner tube and outer tube coaxially mounted on the inner tube, ultrasonic generation means for the inner tube, drive means for the inner tube, an ultrasonic motor connected to the ultrasonic generation means connected to the inner tube, and a drive motor connected to the drive means of the inner tube. The inner tube 16 having an angulated sharp cutting edge 32 at its end 30 (see e.g., FIG. 3a), and the inner tube oscillating in a frequency range of 20.0 cycles per second or more in and through the handpiece for coaxially driving the inner tube for vibratory fragmentation. The same inner tube is piezo-electrically driven or connected to an air pump unit or a peristaltic system that moves the inner tube for a short distance in order to cut the vitreous or other tissues aspirated through an opening of the outer tube so that inner tube utilizes the ultrasonic and cutting coaxially so as to displace the inner tube in a shearing and cutting fashion, like scissors against the edge(s) of the opening, thereby cutting the tissue or fragment semisolid or other polymeric materials, clotted blood or materials, polymeric silicone oil, perfluorocarbon liquids aspirated through the opening in the wall of the outer tube into the inner tube, and the drive means of the inner tube can operate simultaneously or individually.

Figure 3B:
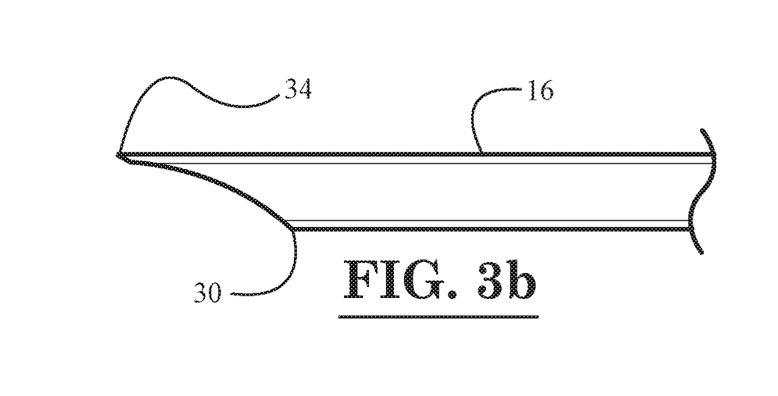
FIG. 3b is a perspective view of a second alternative type of end portion of the inner tube of the vitrectomy instrument of FIG. 1.

In one embodiment, the distal end 30 of the inner tube 16 is angulated (see FIG. 3a), has an oval configuration, or has an elongated part 34 (see FIG. 3b) so that the end of the inner tube is shaped so that it acts as an inner blade against the edges of the outer tube opening which functions as the outer blade of the scissors so that the cutting starts from one side of the inner tube and continues until it covers the entire edges of the opening in the outer wall, thus enhancing the scissor action of the inner tube, and cutting and fragmenting the material aspirated through the opening of the outer tube.

In one embodiment, the instrument is used for a specific surgical need and, for example, might use 40,000 cycles per second frequency for the ultrasonic energy which drives the inner tube, while superimposed on the inner tube is a lower frequency of 5-100 cycles per second of sonic energy. The ultrasonic energy is used for fragmentation of a hard mass of tissue, for example, the lens of the eye, and the sonic energy is used for providing the cutting action. The fragmentation and the cutting actions may occur simultaneously by the same inner tube. Practical operating features such as irrigation, aspiration, cutting, and application of ultrasonic fragmentation energy to the operating site may be applied as required in total or severally by the surgeon.

In one embodiment, the extension of the inner blade forms a blade that can cut or ultrasonically fragment the material aspirated inside the outer tube.

In one embodiment, the instrument operates essentially as a knife, except the blade (i.e., the inner tube) vibrates at a very high frequency (what one would consider to be in the ultrasonic range). An oscillator inside the handle of the instrument drives the vibration. The vibration of the blade (i.e., the inner tube) makes the cutting faster because the vibration of the blade (i.e., the inner tube) also slices the material being cut in addition to the force that the surgeon is applying to the blade. In this embodiment, the instrument essentially operates as an ultrasonic knife with vibrations moving the knife back and forth at a frequency higher than 20,000 cycles per second (i.e., higher than 20,000 Hz). Because the vibrations are applied along the cutting axis of the blade (i.e., the inner tube), the ultrasonic vibrations perform generally the same function as a knife that is manually pushed into a material but, as a result of the ultrasonic vibrations, the instrument does the majority of the cutting work for the surgeon.

In one embodiment, the non-ultrasonic coaxial oscillation of the inner tube has a frequency of 1-5000 per minute or more.

In one embodiment, the diameter of the outer tube is less than one millimeter (mm) in diameter.

In one embodiment, the diameter of the outer tube is less than 0.5 millimeter (mm) in diameter.

In one embodiment, the diameter of the outer tube is less than 0.25 millimeter (mm) in diameter.

In one embodiment, the instrument can be introduced either through the cornea or through the wall of the eye, including the conjunctiva after creating an opening with a 23 gauge needle, a 25 gauge needle, a 27 gauge needle, or lesser gauge needle.

In one embodiment, the opening in the wall of the outer tube permits the material to be aspirated inside the outer tube then to the inner tube where the outer tube is not ultrasonically activated and does not heat the tissue with which it comes into contact at the insertion site of the instrument.

In one embodiment, the opening 28 in the wall of the outer tube 18 is cut in an angular manner (see FIG. 2) to create an angulated sharper edge on the inside edge as compared to the outside edge, but may also have other suitable shapes in alternative embodiments.

In one embodiment, the inner tube can fragment the material when it moves forward passing the opening in the outer wall, and when it moves upward with its ultrasonic action.

In one embodiment, the ultrasonic motion of the inner tube encourages the removal of the fragmented or cut and aspirated or biopsied material inside the inner tube.

In one embodiment, the instrument is provided only with aspiration means and no irrigation means so that the instrument diameter is as small as possible.

In one embodiment, the medical instrument in which the aspiration is performed through the inner tube uses a suction pump or a rotary pump having a syringe, a container to collect the aspirated material, and control means to control aspiration.

In one embodiment, the collected material from the medical instrument is kept sterile away from outside contamination and removed for histological, bacterial, fungal, viral, or polymerase chain reaction (PCR) examination.

In one embodiment, the medical cutting instrument includes a separate irrigation means for supplying irrigation fluid to the surgical space independent from the handpiece to prevent the collapse of the surgical space and maintain a certain pressure in the surgical space.

In one embodiment, the aspiration performed by the medical cutting instrument is accomplished through the side opening near the end of the inner tube.

In one embodiment, the medical cutting instrument includes an outer tube with one or more openings opposite each other where the oscillatory action of the inner tube enhances the cutting and/or fragmenting action of the instrument and can remove more material which is fragmented or cut.

In one embodiment, the medical cutting instrument includes a separate irrigation means for supplying irrigation fluid to the surgical space that is independent from the handpiece. The separate irrigation means being inserted through another small opening made in the wall of the eye and the pressure being controlled using a pressure sensor.

In one embodiment, the medical cutting instrument includes a separate irrigation means for supplying irrigation fluid to the intraocular space placed either through the cornea in the anterior chamber or through the conjunctiva and sclera and choroid into the vitreous cavity.

In one embodiment, the medical cutting instrument includes a small opening on the outer wall with which one can cut the tissue ultrasonically or take a biopsy from the vitreous, retina, choroid, or an intraocular tumor.

In one embodiment, the instrument is equipped with an on-off valve in the supply line.

In one embodiment, the unit is activated with a foot control having a first switch connected to control a valve, a second switch for controlling a pump, and a third switch for controlling the ultrasonic generator.

In one embodiment, the instrument has drive means mounted directly in an ultrasonic transformation horn portion of the ultrasonic motor.

In one embodiment, the operating tool is removable from the handpiece.

In one embodiment, a separate ultrasonic generator and drive means is provided, which includes means for changing the applied frequencies, and their amplitude to match variations in the cutting tube, and vibrating tool.

It is readily apparent that the aforedescribed vitrectomy instrument and the vitrectomy system including the same offer numerous advantages. First, the vitrectomy instrument facilitates the cutting of tissue or vitreous without the undesirable excessive heating and resulting burning of the tissue surrounding the instrument during the procedure. Secondly, the vitrectomy instrument does not require the use of a plastic insulating sleeve to be placed around the needle of the instrument, thus permits a small incision to be made for the insertion of the instrument. Finally, the vitrectomy system described above, which includes the vitrectomy instrument, provides separate irrigation means so as to minimize the size of the needle of the vitrectomy instrument.

Advantageously, the aforedescribed vitrectomy system permits a small self-healing, non-sutured incision to be made for the insertion of the instrument. Also, combining the ultrasound and cutting in the inner tube enhances both cutting and fragmentation, and also enhances aspiration of the tissue to be removed from the tube and prevents the burning of the tissue at the entrance to the eye cavity or other location where this instrument is used. The aforedescribed instrument can be used both for vitrectomy and lens extraction or biopsy of the vitreous or tissue of the retina or the choroid, or for a biopsy of the breast, brain, prostate, etc. The ultrasonic function can be activated with the cutting action or independently.

Figure 5A:
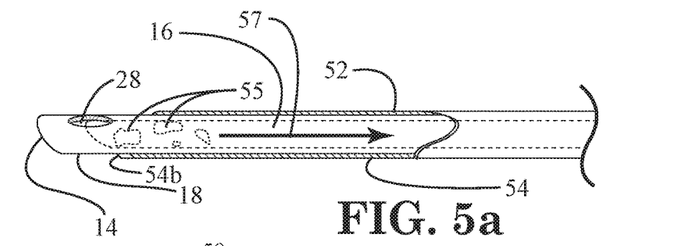
FIG. 5a is a diagrammatic partial perspective view of a combined vitreous cutter and sleeve, according to an embodiment of the invention.
Figure 5B:
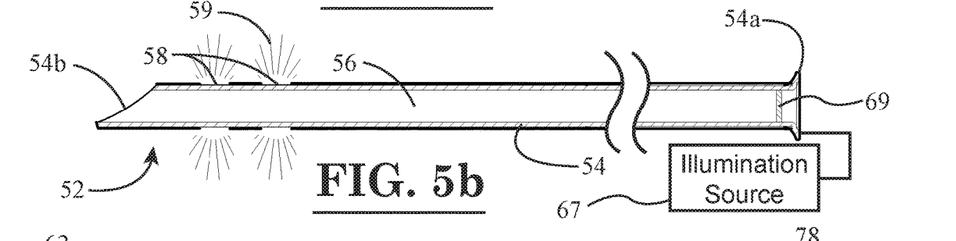
FIG. 5b is a diagrammatic perspective view of a support sleeve for a vitrectomy instrument, according to another embodiment of the invention.

Now, with reference to FIGS. 5a and 5b, an illustrative embodiment of a support sleeve 52 for a vitrectomy instrument will be described. As best shown in FIG. 5b, the support sleeve 52 includes an elongate tubular body 54 having a first end 54a and a second end 54b disposed opposite to the first end 54a. The elongate tubular body 54 further includes a peripheral sidewall (i.e., the tubular sidewall in FIG. 5b) and a central cylindrical passageway 56 disposed through the elongate tubular body 54. The central cylindrical passageway 56 of the elongate tubular body 54 is configured to receive a vitrectomy instrument therein (e.g., instrument shown in FIG. 5a with inner tube 16 and outer tube 18), and at least a portion of the elongate tubular body 54 is formed from a material that is transparent to visible light (as will be described in more detail hereinafter). Referring again to FIGS. 5a and 5b, it can be seen that the support sleeve 52 may be configured to emit light from an illumination source 67 (e.g., fiber optic device). For example, as shown in FIGS. 5a and 5b, light may be emitted from a location near the second end 54b of the support sleeve 52 (i.e., in the illustrative embodiment, the tubular sidewall of the sleeve 52 may be painted opaque to prevent the transfer of light therethrough, while the second end 54b of the sleeve 52 may be unpainted so as to allow the emission of light therefrom). Also, as shown in FIG. 5b, selected portions 58 of the tubular sidewall of the sleeve 52 may be left unpainted so as to allow the passage of light 59 therethrough (i.e., the unpainted portions 58 of the tubular sidewall act as light windows). For example, in the illustrative embodiment, the opaque coating or paint may comprise a thin layer of black paint.

As shown in FIG. 5b, the sleeve 52 may include a pierceable membrane 69 near the entrance of the elongate tubular body 54 of the sleeve 52 is configured to create a substantially liquid-tight seal between an outer peripheral surface of the vitreous cutter and an inner peripheral surface of the peripheral sidewall of the vitreous cutter sleeve 52 after the vitreous cutter has penetrated the pierceable membrane 69.

In the illustrative embodiment, the sleeve 52 may be illuminated by any standard illuminating system providing the needed light intensity. The illumination device may be disposed inside or outside the sleeve 52, or in any suitable position relative to the sleeve 52. The illumination device is preferably connected to the sleeve 52 at a site that does not enter the body. It can either illuminate the entire sleeve 52, or the outer surface of sleeve 52 can be coated with a thin layer of black material (see FIGS. 5a and 5b), thus leaving only the tip at the second end 54b of the sleeve 52, or an area 58 adjacent the tip free to permit the light to exit the sleeve 52. The illumination permits visualization of the tissue, once the needle has penetrated a soft tissue and can be followed by observing its path and the position of the needle tip. This eliminates guessing how far a needle has penetrated the tissue.

As depicted in FIG. 5b, the first end 54a of the elongate tubular body 54 of the support sleeve 52 comprises a flared end portion configured to prevent the support sleeve 52 from entering too deep into the eye. That is, the peripheral flange of the flared end portion of the elongate tubular body 54 prevents the over-insertion of the support sleeve 52 into the eye. Obviously, the over-insertion of the sleeve 52 into the eye of the patient could pose a substantial safety risk to the patient. For example, without the flared end portion thereon, the first end 54a of the support sleeve 52 could potentially pass completely through its insertion hole in the eye, and possibly become lodged inside the eye of the patient.

As shown in FIG. 5a, the support sleeve 52 may be provided as part of a combined vitreous cutter and sleeve assembly. Alternatively, as shown in FIG. 5b, the support sleeve 52 may be provided as an independent sleeve apart from the vitrectomy instrument. In the combined vitreous cutter and sleeve assembly of FIG. 5a, the support sleeve 52 is configured to contain the closed end tip 14 of the vitrectomy instrument when the vitrectomy instrument is being removed from the eye so as to prevent the closed end tip 14 from contacting and contaminating healthy tissue in the eye. That is, one advantage of the combination vitreous cutter and sleeve is that both instruments can be removed from the eye as a one-piece unit to prevent contamination resulting from the tip 14 of the vitreous cutter. Another advantage of the combination vitreous cutter and sleeve is that both instruments also can be inserted into the eye as a one-piece unit. When inserted as a one-piece unit into the eye, the combination vitreous cutter and sleeve is capable of passing through the conjunctiva, sclera, etc. without the need for an incision beforehand and the subsequent separate insertion of the cutter into the incision. In one or more embodiments, the combination vitreous cutter and sleeve may be preassembled as a one-piece unit so as to maximize ease of use and sterility.

In FIGS. 5a and 5b, it can be seen that the second end 54b of the elongate tubular body 54 of the support sleeve 52 comprises a pointed tip configured to cut through tissue of the eye. That is, when the sleeve 52 is first inserted into the eye, the pointed tip of sleeve 52 readily pierces the outer layer of the eye (i.e., the sclera of the eye) so that the sleeve 52 can be easily placed in the vitreous cavity of the eye. In the illustrative embodiment of FIGS. 5a and 5b, it can be seen that the pointed tip of sleeve 52 has a generally tapered geometry. In FIG. 5a, cut tissue 55 is shown being aspirated by the vitreous cutter (as diagrammatically indicated by the arrow 57 in FIG. 5a).

In the illustrative embodiment, the elongate tubular body 54 of the support sleeve 52 may be formed from a material is transparent to visible light from 400-800 nanometers (nm). For example, in the illustrative embodiment, the material forming the body 54 of the support sleeve 52 may comprise one of: (i) metal glass, (ii) amorphous glass, (iii) palladium alloy, (iv) zirconium alloy, (v) aluminum nitryloxyde, and (vi) stainless steel. Advantageously, the use of a material, such as metal glass, for the body 54 of the support sleeve 52 provides a strong, rigid support for the needle of vitrectomy instrument that is also able to conduct light.

Figure 6A:
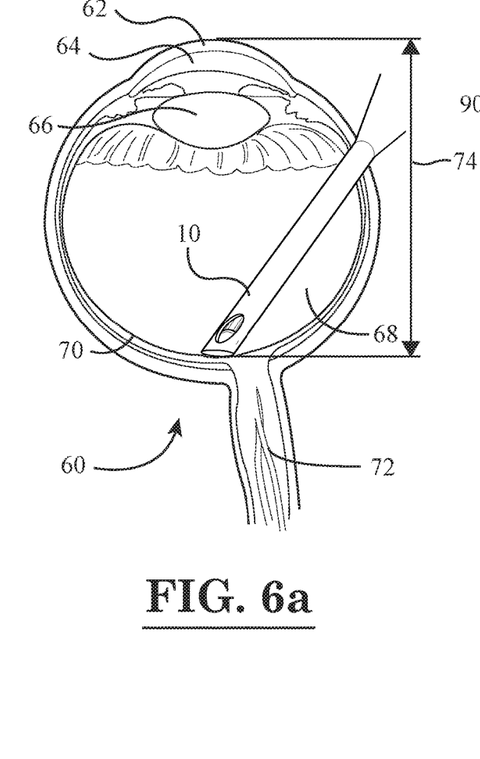
FIG. 6a is a side cross-sectional view of a normal eye having a surgical procedure performed thereon by a vitrectomy instrument where the instrument reaches the posterior portion of the eye.
Figure 6B:
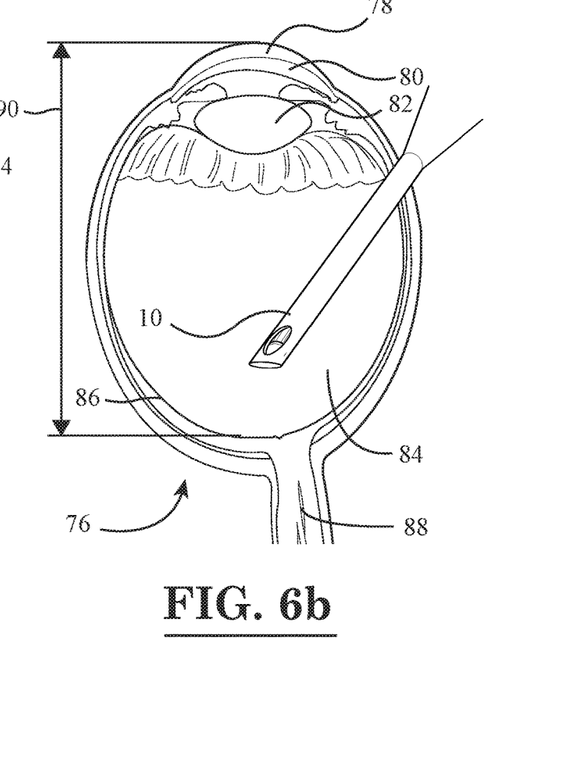
FIG. 6b is a side cross-sectional view of a myopic eye having a surgical procedure performed thereon by a vitrectomy instrument where the instrument does not reach the posterior portion of the eye.

Next, referring to FIGS. 6a and 6b, a vitrectomy instrument 10 is shown disposed in both a normal eye 60 (i.e., FIG. 6a) and a myopic eye 76 (i.e., FIG. 6b). As shown in FIG. 6a, the illustrative normal eye 60 has a diameter 74 of approximately twenty-four (24) millimeters, and includes a cornea 62, an anterior chamber 64, a lens 66, a vitreous cavity 68, a retina 70, and an optic nerve 72. In FIG. 6a, it can be seen that the needle of the vitrectomy instrument 10 is able to reach the retina 70 at the back of the normal eye 60. As shown in FIG. 6b, the illustrative myopic eye 76 has a diameter 90 in the range between approximately twenty-four (24) millimeters and approximately thirty-six (36) millimeters, and includes a cornea 78, an anterior chamber 80, a lens 82, a vitreous cavity 84, a retina 86, and an optic nerve 88. In FIG. 6b, it can be seen that the needle of the vitrectomy instrument 10 is unable to reach the retina 86 at the back of the myopic eye 76.

Figure 7:
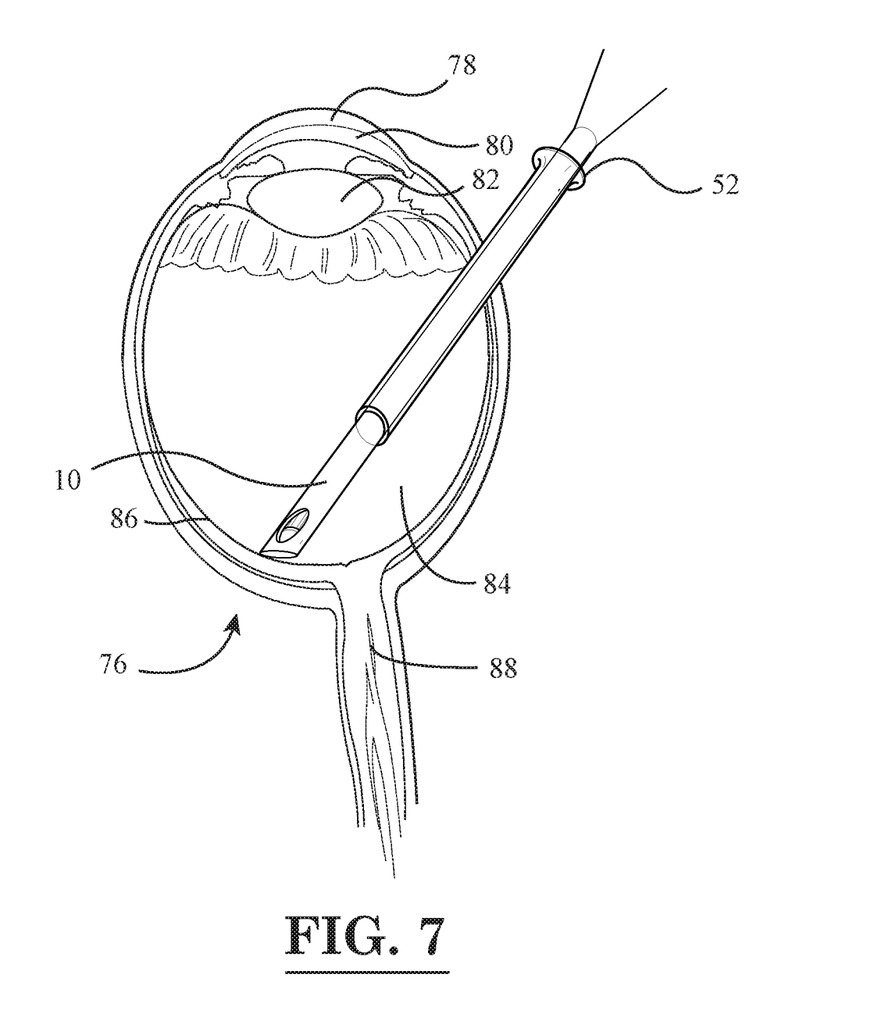
FIG. 7 is a side cross-sectional view of a myopic eye having a surgical procedure performed thereon by a vitrectomy instrument supported within a support sleeve, whereby the instrument is able to reach the posterior portion of the eye.

In one or more embodiments, the support sleeve 52 may be formed from a highly rigid material, such as metal glass, so as to render the vitrectomy instrument 10 inflexible when using the instrument 10 on a long myopic eye of more than 30 millimeters (mm) in length (e.g., refer to the eye 76 depicted in FIG. 7). Advantageously, in the combined vitreous cutter and sleeve assembly, the rigid support sleeve 52 compensates for the flexibility of the long needle 12 of the vitrectomy instrument 10 so that the long flexible needle 12 does not substantially deflect and/or deform when the needle 12 is inserted in the eye 60, 76.

In one or more embodiments, a combined vitreous cutter and sleeve assembly is provided that includes a support sleeve tightly connected to the vitrectomy cutter shaft, and that is formed from a material that is harder than stainless steel (e.g., metal glass) so as to eliminate the shortcomings associated with the flexible nature of the vitrectomy cutter shaft (e.g., the stainless steel or other material forming the vitrectomy cutter outer tube may have a Brinell hardness of between 160 and 300, whereas the metal glass or other material forming the elongate tubular body of the support sleeve may have a Brinell hardness of greater than 900). Also, the support sleeve may include illumination means for projecting light through the shaft of the sleeve so as to eliminate the need for additional incisions to be made in the eye for fiber optic illumination.

In one or more embodiments, the support sleeve may be made from various composites, such as metal glass, amorphous glass, or similar alloys such as palladium alloy and zirconium alloy, aluminum oxynitride (AlON), magnesium aluminate spinel (spinel), and single crystal aluminum oxide (sapphire), aluminum oxynitride spinel (Al23O27N5) or any other suitable material. These compounds are tougher than the presently used stainless steel for conventional vitrectomy cutters or needles. These compounds are also transparent to visible light from 400-800 nm, such that it is possible to direct the light for visualization through the body of the sleeve without increasing the diameter of the instrument or the need for an additional incision for a fiber optic. Similarly, aluminum nitryloxyde is a transparent polycrystalline ceramic structure composed of aluminum and oxygen. This compound is harder than fused silica glass and sapphire or magnesium aluminum. It is lightweight and resistant to damage by oxidation or radiation. The manufacturing technique is known and the sleeve may be formed using conventional ceramic powder or 3-D printing.

In one embodiment, the vitrectomy instrument is contained within a support sleeve formed from metal glass, and the vitrectomy instrument comprises a needle that is vibrated at a low ultrasonic frequency in a range between 10,000 Hz and 20,000 Hz so as to prevent the excessive heating of tissue surrounding the needle.

In one embodiment, the support sleeve reinforces the vitreous cutter along the length of the intraocular portion of the vitreous cutter so that the length of the cutter may be increased to a length of up to 36-38 mm or more in order to reach posterior segment in a large myopic eye with ease, without the need to press on the wall of the eye or distort it any way.

In one embodiment, the sleeve reinforces the resilience of the cutter, and has at least a length of 18-26 mm, or 26-32 mm or more, and the length of the intraocular portion of the vitreous cutter is up to 36-38 mm or more in order to reach posterior segment in a large myopic eye with ease, without the need to press on the wall of the eye or distort it any way.

In one embodiment, a vitreous cutter instrument is positioned inside an independent sleeve with a length 18-30 mm, which reaches down to the cutting edge of the hole in the outer wall of the cutter without covering the hole so as to provide support to the shaft of the cutter.

In one embodiment, the shaft of a vitreous cutting instrument is positioned inside a sleeve that is independent from the cutter in which the cutter's shaft is placed in like a hand and glove relationship, and the sleeve reaches down to the cutting edge of the hole in the outer wall of the cutter without covering the hole, and the sleeve has a length of at least 15-20 mm.

In one embodiment, the sleeve has a diameter of a 25-30 gauge needle, and is made of metal glass.

In one embodiment, there is a sleeve with 3 to 4 tubes inside each other supporting greater than 90% of the length of the shaft of the cutter having an outer diameter of a 27-30 gauge needle.

In one embodiment, there is a sleeve with three tubes comprising a 25 gauge outer tube, a 27 gauge middle tube, and a 30 gauge inner tube where the cutter and sleeve are in intimate contact with one another without preventing each other's motion.

In one embodiment, there is a sleeve with three tubes comprising a 27 gauge outer tube, a 29 gauge middle tube, and a 30 or 32 gauge inner tube.

In one embodiment, the instrument is inserted through the conjunctiva in the eye and the incision is self-sealing without the need for sutures.

In one embodiment, there are only two tubes with an outer sleeve and an inner needle for inserting through the conjunctiva and the sclera to the vitreous cavity where the inner needle has an irrigation function made of a metal and the outer sleeve is made of metal glass and acts as an illumination device. In this embodiment, the inner needle may be in the form of a single tube with an open end, and the outer sleeve stabilizes the tube and illuminates the area being irrigated in the eye.

In one embodiment, the support sleeve reinforces the vitreous cutter along the length of the intraocular portion of the vitreous cutter so that the cutter may be increased to a length of up to 36-40 mm or more in order to reach a breast or prostate tumor with ease without bending to obtain a tissue biopsy.

It is readily apparent that the aforedescribed vitrectomy instrument supporting sleeve and the system including the same offer numerous advantages. First, the support sleeve for the vitrectomy instrument structurally supports the flexible needle of the instrument so as to prevent the needle from moving and/or bending during surgery. Secondly, the support sleeve enables a vitrectomy instrument with a long needle to be more effectively used in myopic eyes, which have a longer axial length than normal eyes. Finally, the vitrectomy system described herein includes the rigid support sleeve for enabling a vitrectomy instrument with a long needle to be used in an eye (e.g., myopic eye) without excessive deflection and/or bending thereof.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A vitrectomy instrument, comprising:
a handpiece having a housing and an intraocular portion with an outer tube and an inner tube coaxially disposed in the outer tube, the inner tube having a distal end and a proximal end oppositely disposed relative to the distal end, the inner tube being slidably displaceable relative to the outer tube, the outer tube having a diameter that is less than 1.0 millimeter, the intraocular portion having a length up to 40 millimeters, and the inner tube having a central cutting axis;
a cutting power generator operatively coupled to the inner tube, the cutting power generator configured to reciprocably drive the inner tube for shearing tissue, vitreous, and/or silicone oil, the cutting power generator including an energizing coil and an iron core driven by the energizing coil, the iron core comprising a central opening extending longitudinally through the iron core, the proximal end of the inner tube being received in one end of the central opening of the iron core; and
an ultrasonic generator operatively coupled to the inner tube, the ultrasonic generator including at least one piezoelectric disc member vibrationally-isolated from the housing of the vitrectomy instrument by a damping member, the ultrasonic generator configured to vibrate the inner tube for vibratory fragmentation and/or cutting of the tissue, the vitreous, and/or the silicone oil, the at least one piezoelectric disc member of the ultrasonic generator being axially aligned with the cutting power generator on the central cutting axis of the inner tube;
wherein the cutting power generator is disposed closer to the distal end of the inner tube than the ultrasonic generator; and
further comprising an aspiration tube having a distal end and a proximal end oppositely disposed relative to the distal end, the distal end of the aspiration tube being received in an end of the central opening of the iron core that is opposite to the end of the central opening that receives the proximal end of the inner tube, the aspiration tube configured to transport cut tissue and/or cut vitreous being discharged from the handpiece, and the distal end of the aspiration tube being spaced apart from the proximal end of the inner tube in the central opening of the iron core by a gap.

2. The vitrectomy instrument according to claim 1, wherein the outer tube comprises a body and a closed end tip, the body of the outer tube including a sidewall extending in an axial direction from the closed end tip, the body of the outer tube defining a linear passageway closed at a distal end by the closed end tip; and
wherein the outer tube further comprises an opening disposed in the sidewall of the body, the opening being disposed proximate to the closed end tip of the outer tube, and the opening being configured to enable cutting of the tissue, the vitreous, and/or the silicone oil.

3. The vitrectomy instrument according to claim 1, wherein the cutting power generator is separate from the ultrasonic generator such that the cutting power generator and the ultrasonic generator are capable of being simultaneously or individually operated.

4. The vitrectomy instrument according to claim 1, wherein the ultrasonic generator is configured to produce signals in a frequency range of 20,000 cycles per second or greater for the vibratory fragmentation and/or cutting of the tissue, the vitreous, and/or the silicone oil by the inner tube.

5. The vitrectomy instrument according to claim 1, further comprising an aspiration device operatively coupled to the aspiration tube, the aspiration device configured to generate an aspiration force for removing the cut tissue and/or cut vitreous through the inner tube.

6. The vitrectomy instrument according to claim 5, wherein the aspiration device comprises a suction pump or a rotary roller peristaltic pump for generating the aspiration force for removing the cut tissue and/or the cut vitreous through the inner tube of the handpiece.

7. The vitrectomy instrument according to claim 1, wherein the handpiece is not provided with irrigation means so as to enable the diameter of the handpiece to be made as small as possible.

* * * * *